United States Patent

Eno et al.

[11] Patent Number: 6,053,942
[45] Date of Patent: Apr. 25, 2000

[54] TRANSMYOCARDIAL IMPLANT WITH CORONARY STENT

[75] Inventors: Robert A. Eno, Plymouth, Minn.;
Donald C. Harrison, Cincinnati, Ohio;
Jerry Griffin, Chicago, Ill.

[73] Assignee: Heartstent Corporation, St. Paul, Minn.

[21] Appl. No.: 09/135,879

[22] Filed: Aug. 18, 1998

[51] Int. Cl.[7] .................................. A61F 2/06; A61F 2/04
[52] U.S. Cl. ................................................ 623/1.15; 623/12
[58] Field of Search ......................... 623/1, 3, 12, 1.1, 623/1.15; 606/198, 108; 628/898

[56] References Cited

U.S. PATENT DOCUMENTS

| | | | |
|---|---|---|---|
| 5,064,435 | 11/1991 | Porter | 62/12 X |
| 5,562,727 | 10/1996 | Turk et al. | 623/1 |
| 5,655,548 | 8/1997 | Nelson et al. | 128/898 X |
| 5,667,523 | 9/1997 | Bynon et al. | 606/198 X |
| 5,755,682 | 5/1998 | Knudson et al. | |
| 5,817,100 | 10/1998 | Igaki | 606/108 X |
| 5,824,071 | 10/1998 | Nelson et al. | 623/3 X |
| 5,984,956 | 11/1999 | Tweden et al. | |

FOREIGN PATENT DOCUMENTS

| | | |
|---|---|---|
| WO 98/06356 | 2/1998 | WIPO . |
| WO 99/17683 | 4/1999 | WIPO . |

*Primary Examiner*—Michael J. Milano
*Assistant Examiner*—Hieu Phan
*Attorney, Agent, or Firm*—Merchant & Gould P.C.

[57] ABSTRACT

A transmyocardial implant includes a hollow rigid conduit having a first portion and a second portion. The first portion is sized to be larger than an initial lumen diameter of a coronary vessel. The first portion is smaller than an enlarged lumen diameter. The second portion is sized to extend from the first portion and through a myocardium into a heart chamber. The implant further includes a stent having a first stent diameter and adapted to be enlarged to an enlarged second stent diameter. In the first stent diameter, the stent is sized to be inserted into the initial lumen diameter. In the second diameter, the stent is sized to dilate the lumen to the enlarged lumen diameter. When the stent is at the second stent diameter, the stent has an internal diameter sized to receive the first portion of the conduit.

6 Claims, 4 Drawing Sheets

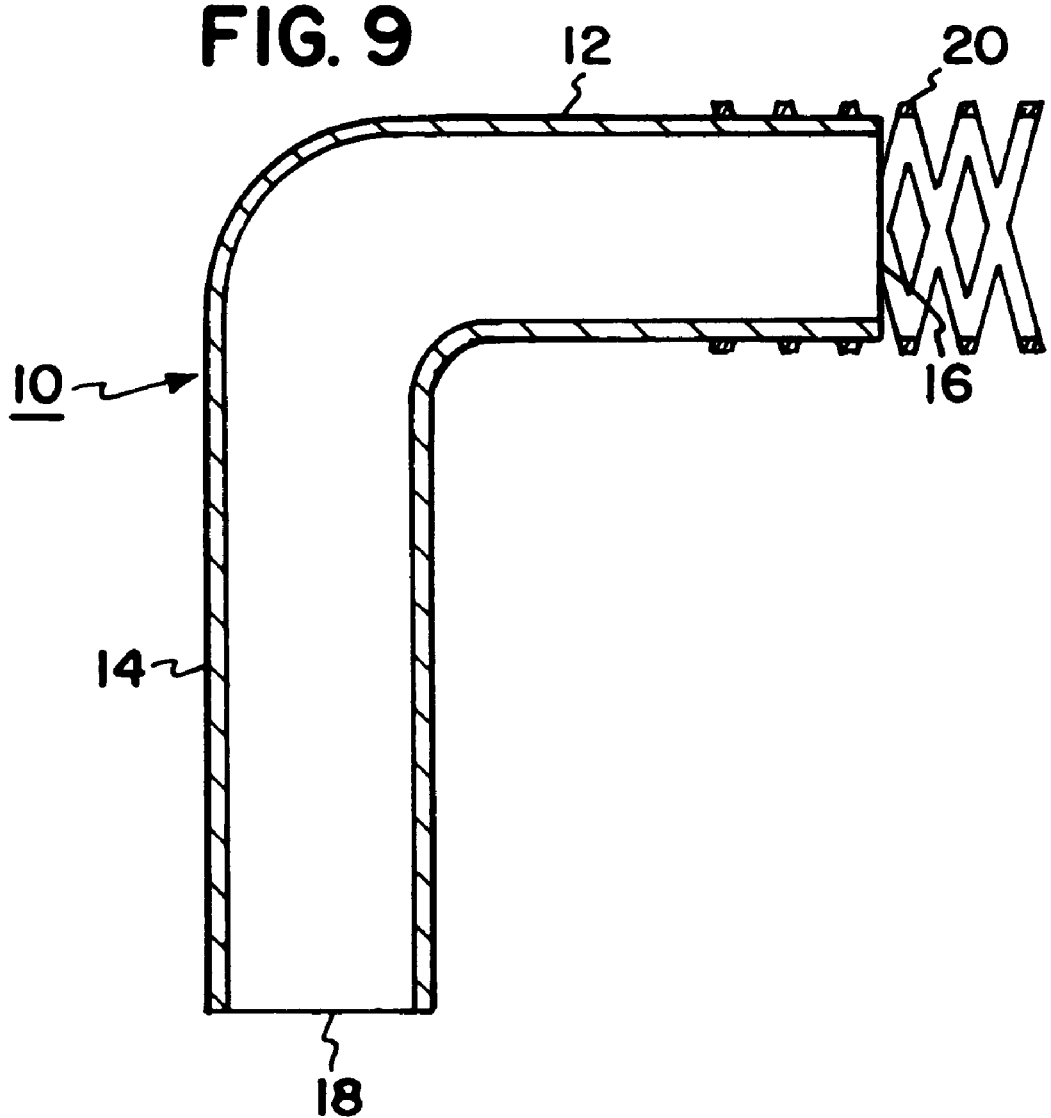

6,053,942

TRANSMYOCARDIAL IMPLANT WITH CORONARY STENT

BACKGROUND OF THE INVENTION

1. Field of the Invention

This invention pertains to an implant for passing blood flow directly between a chamber of the heart and a coronary vessel. More particularly, this invention pertains to such an implant with an enhanced design for facilitating placement of a transmyocardial conduit into a coronary vessel.

2. Description of the Prior Art

Commonly assigned U.S. Pat. No. 5,755,682 and PCT International Publication No. WO 98/06356 teach an implant for defining a blood flow conduit directly from a chamber of the heart to a lumen of a coronary vessel. An embodiment disclosed in the aforementioned patent and application teaches an L-shaped implant The implant is a conduit having one leg sized to be received within a lumen of a coronary artery and a second leg sized to pass through the myocardium and extend into the left ventricle of the heart. As disclosed in the above-referenced patent and application, the conduit remains open for blood flow to pass through the conduit during both systole and diastole. The conduit penetrates into the left ventricle in order to prevent tissue growth and occlusions over an opening of the conduit Commonly assigned and co-pending U.S. patent application Ser. No. 08/944,313 filed Oct. 6, 1997, entitled "Transmyocardial Implant", and filed in the name of inventors Katherine S. Tweden, Guy P. Vanney and Thomas L. Odland, teaches an implant such as that shown in the aforementioned patent application with an enhanced fixation structure. The enhanced fixation structure includes a fabric fixation structure. The enhanced fixation structure includes a fabric surrounding at least a portion of the conduit to facilitate tissue growth on the exterior of the implant Implants such as those shown in the aforementioned patent and applications include a portion to be placed within a coronary vessel and a portion to be placed within the myocardium. When placing a portion of the implant in the coronary vessel, the vessel is incised a length sufficient to insert the implant When placed within the coronary vessel, the implant discharges flow axially into the vessel.

When placing an implant, a portion of the coronary artery is dissected. The dissected portion is incised and the vessel portion of the implant is inserted into the lumen. A stay suture secures the artery to the implant. The stay suture is spaced around the artery and vessel portion a distanced space from the open end of the vessel portion.

In a preferred embodiment, the implant is rigid. After an artery is incised to receive an implant, the artery may collapse in diameter. Also, the artery may have an initial diameter smaller than the outside diameter of the implant The implant may be inserted into the artery to expand the artery. However, this insertion may include a rubbing against the fragile artery wall resulting in damage.

SUMMARY OF THE INVENTION

According to a preferred embodiment of the present invention, a transmyocardial implant is disclosed for establishing a blood flow path through a myocardium between a heart chamber and a lumen of a coronary vessel residing on an exterior of the heart The implant includes a hollow rigid conduit having a first portion and a second portion. The first portion is sized to be larger than an initial lumen diameter and smaller than an enlarged lumen diameter. The second portion is sized to extend from the first portion and through the myocardium into a heart chamber. The implant further includes a stent having a first stent diameter and adapted to be enlarged to an enlarged second stent diameter. In the first stent diameter, the stent is sized to be inserted into the initial lumen diameter. In the second diameter, the stent is sized to dilate the lumen to the enlarged lumen diameter. When the stent is at the second stent diameter, the stent has an internal diameter sized to receive the first portion of the conduit.

BRIEF DESCRIPTION OF THE DRAWINGS

FIG. 9 is an alternative embodiment to the embodiment depicted in FIG. 8.

DESCRIPTION OF THE PREFERRED EMBODIMENT

Figure 1:
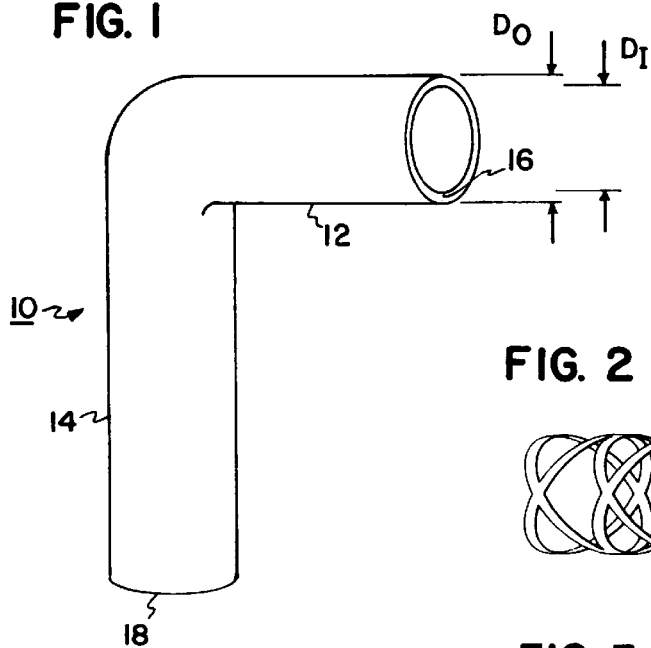
FIG. 1 is a perspective view of a transmyocardial conduit.

With initial reference to FIG. 1, a transmyocardial conduit 10 is shown in the form of an L-shaped rigid tube. The conduit 10 may be formed of titanium or other rigid biocompatible material such as pyrolytic carbon or titanium coated with pyrolytic carbon. The material of the conduit 10 is preferably a rigid material in order to withstand contraction forces of the myocardium. By way of example, the tube will have an outside diameter $D_O$ of about 2.5 millimeters and an internal diameter $D_I$ of about 2.0 millimeters to provide a wall thickness of about 0.25 millimeters.

Figure 4:
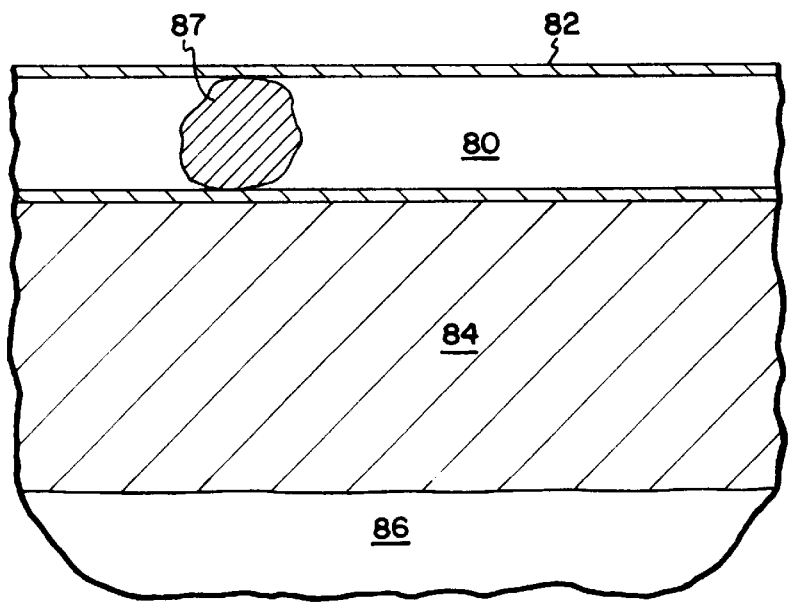
FIG. 4 is a side sectional schematic view showing an occluded artery on a heart wall.

The conduit 10 has a first portion (or vessel end) 12 sized to be received within the lumen of a coronary vessel such as the lumen 80 of a coronary artery 82 illustrated in FIG. 4. The conduit 10 has a second portion (or myocardium end) 14 extending at a right angle to the axis of portion 12. The second portion 14 is sized to extend from the coronary artery 82 directly through the myocardium 84 and protrude into the left ventricle 86 of a patient's heart. The second portion 14 is sized to have a length sufficient for the portion 14 to protrude into the left ventricle 86.

The vessel end 12 has a first opening 16. The myocardium end 14 has a second opening 18 in communication with an interior 21 of the conduit 10. Therefore, blood can freely flow through the conduit 10 between the left ventricle 86 and the lumen 80 of the coronary artery 82. Blood flows axially out of opening 16 parallel with the axis of lumen 80.

As discussed more fully in the aforementioned commonly assigned and copending U.S. patent application Ser. No. 08/944,313, the portion 14 may be provided with tissuegrowth-inducing material (not shown in the present application) such as a polyester sleeve to immobilize the conduit 10 within the myocardium 84.

The implant of the present invention further includes a stent 20. The stent 20 is a tubular member of lattice formed of biocompatible material. The stent 20 has an initial diameter $D_1$ sized smaller than the conduit outer diameter $D_O$ and further sized for the stent 20 to be inserted into lumen 80. The stent 20 is expandable to an enlarged second diameter $D_2$ sized to expand the artery 82. Further, the stent 20 is sized to receive the second portion 12 of the conduit 10 when the stent 20 is expanded to the enlarged second diameter $D_2$. It will be appreciated that coronary stents such as stent 20 are commercially available in a wide variety of sizes, shapes, materials and mode of expansion (e.g., self-expanding or balloon expandable). Stent 20 can be any member whose outside dimensions expand to enlarge lumen 80 and whose internal dimensions permit insertion of the vessel portion 12.

Figure 5:
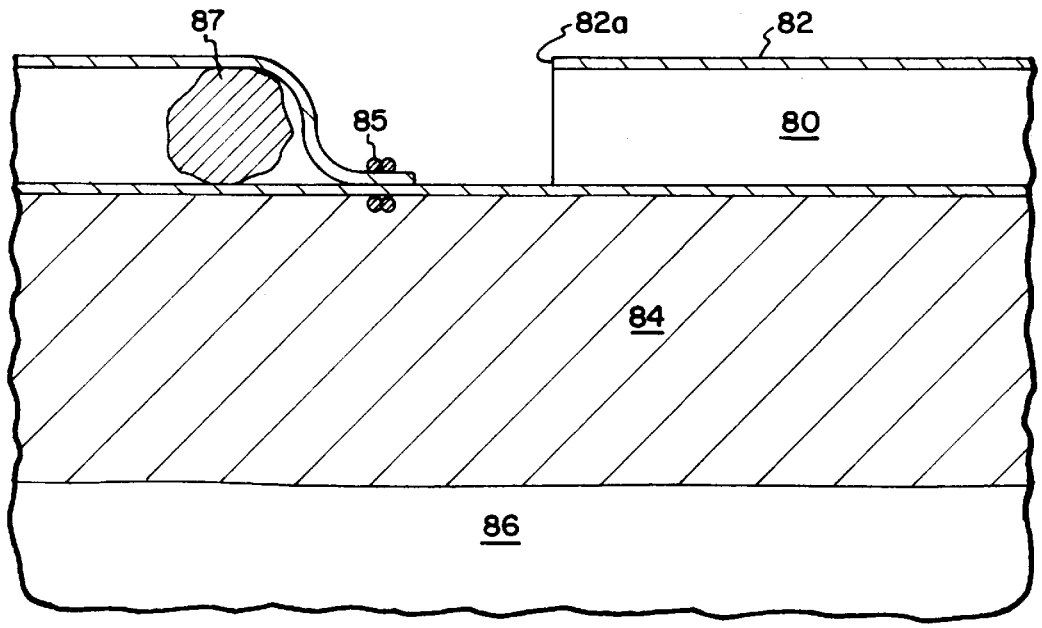
FIG. 5 is the view of FIG. 4 following dissection of a portion of the artery, ligation distal to the obstruction and incision of the artery distal to the ligation.

With reference to FIG. 5, a surgeon dissects a portion of the artery 82 away from the myocardium 84. The surgeon ligates the artery 82 distal to an obstruction 87 with sutures 85. The surgeon then forms an incision through the artery 82 distal to the ligating suture 85.

Figure 2:
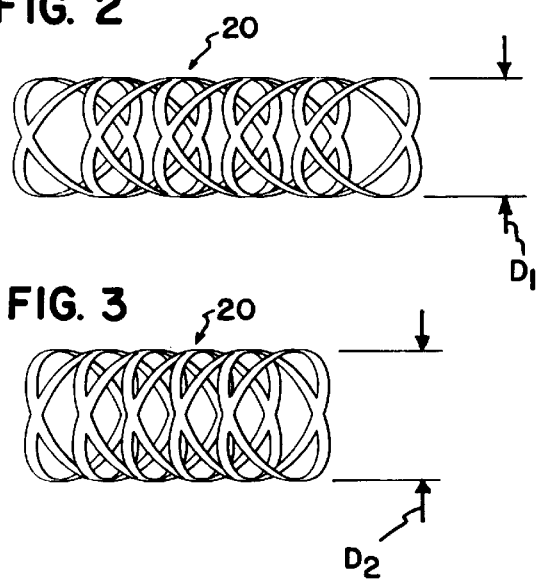
FIG. 2 is a perspective view of stent shown in a reduced first diameter.
Figure 3:
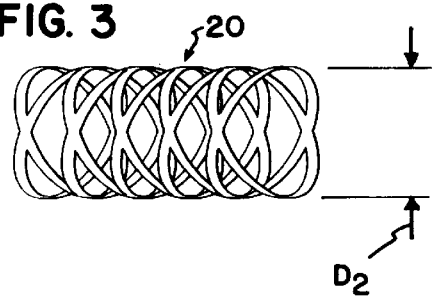
FIG. 3 is the view of FIG. 2 showing the stent in an enlarged second diameter.
Figure 6:
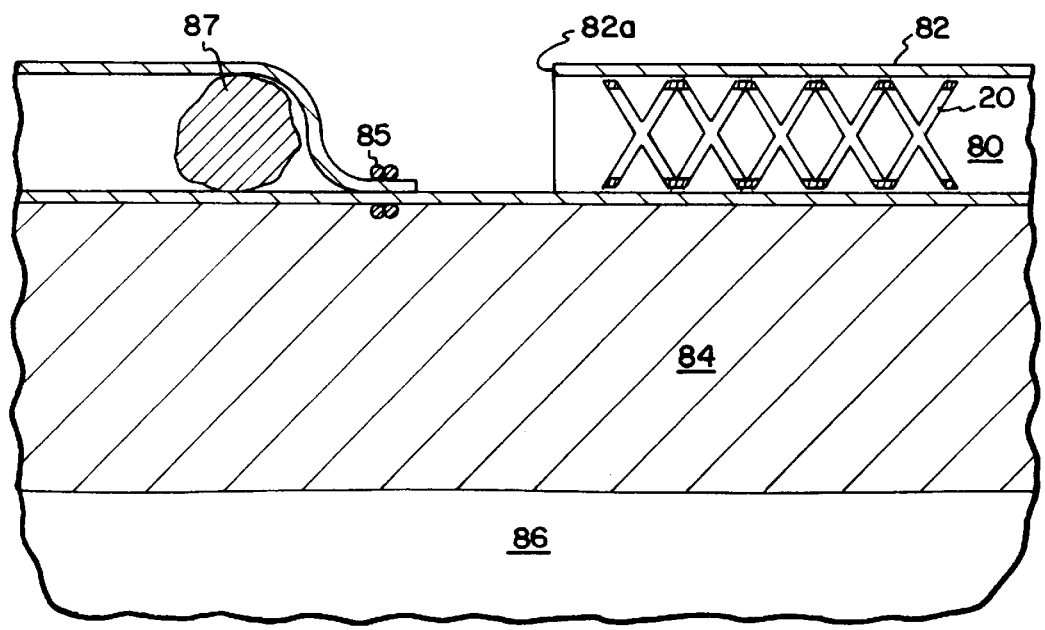
FIG. 6 is the view of FIG. 5 following placement of the reduced diameter stent of FIG. 2 into the artery.
Figure 7:
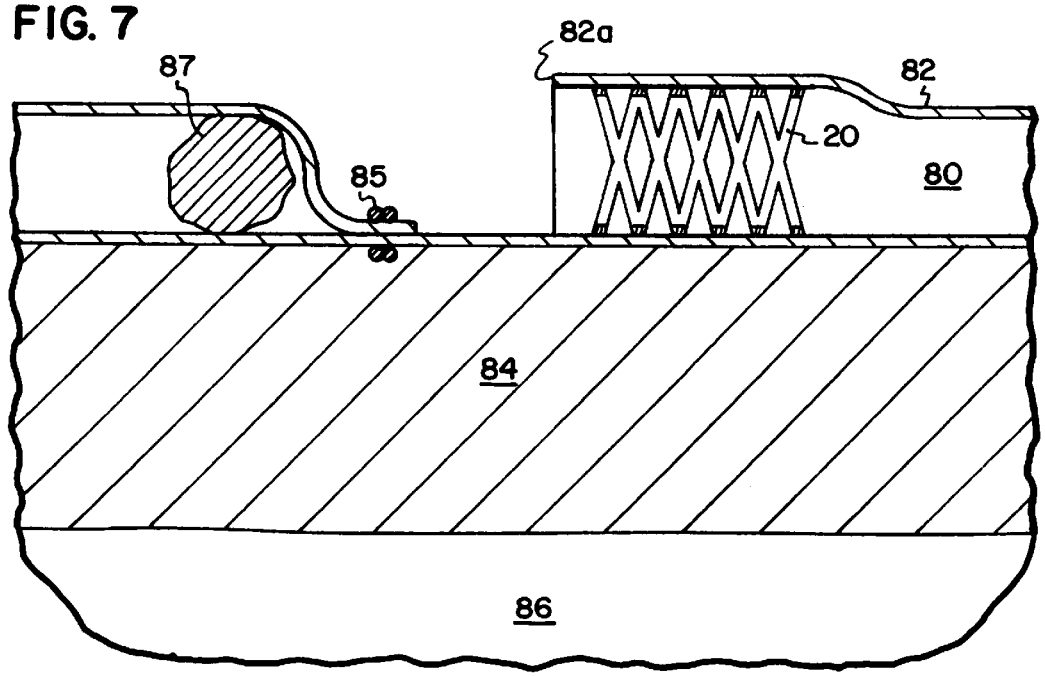
FIG. 7 is the view of FIG. 6 following expansion of the stent to the enlarged second diameter.

The stent 20 (in the reduced diameter $D_1$ of FIG. 2) is slipped into the lumen 80 through the open end 82a of the artery 82 (FIG. 6). The stent 20 is expanded to the enlarged diameter $D_2$. The expansion causes a corresponding expansion of the lumen 80 at the incised artery end 82a (FIG. 7).

Figure 8:
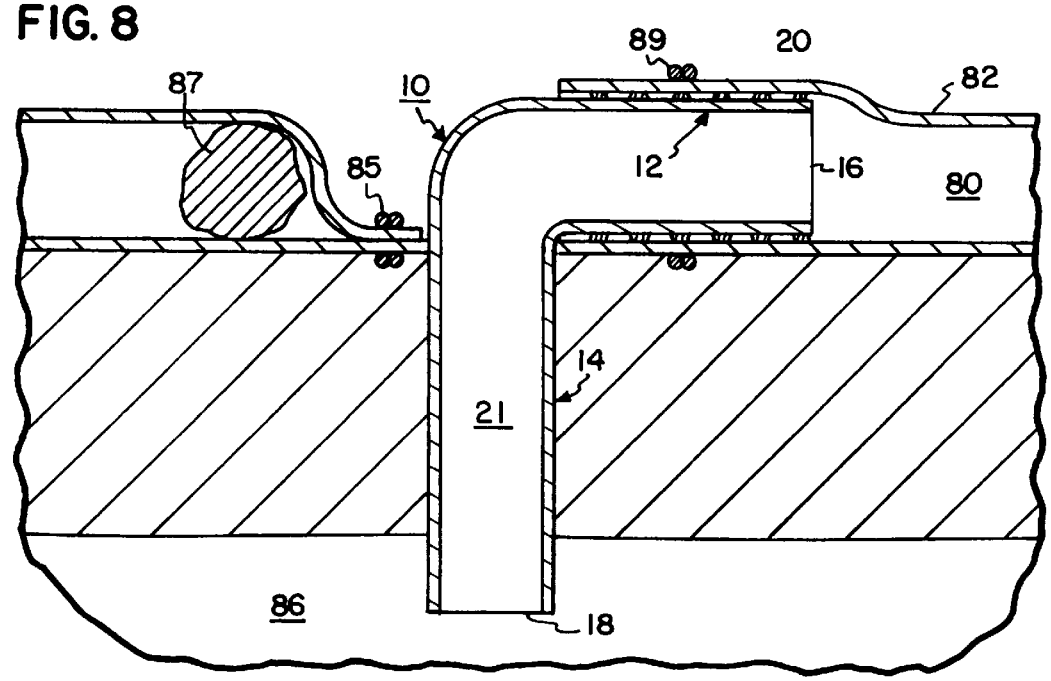
FIG. 8 is the view of FIG. 7 following placement of the implant of FIG. 1.

The conduit 10 is placed by inserting the second portion 14 through the myocardium 84 with open end 18 in communication with the left ventricle 86. The first portion 12 is inserted into the enlarged stent 20 (FIG. 8). Stay sutures 89 are placed 15 around the artery 82 overlying the stent 20 and vessel portion 12. The stay sutures 89 are tightened to crimp the artery 82, stent 20 and vessel portion 12 together.

In FIG. 8, the stent 20 is shown as being co-terminus with the vessel portion 12 (i.e., an end of the stent 20 is aligned with the open end 16). FIG. 9 illustrates an alternative where the stent 20 extends beyond the open end 16.

With the structure thus described, the artery 82 is enlarged to receive the vessel portion 12. The enlargement results from radial expansion forces due to the expansion of the stent 20. This enlargement minimizes arterial damage.

From the foregoing, the invention has been described in a preferred embodiment Modifications and equivalents of the disclosed concepts are intended to be included within the scope of the claims.

What is claimed is:

1. A transmyocardial implant for establishing a blood flow path through a myocardium between a heart chamber and a lumen of a coronary vessel residing on an exterior of said myocardium where the vessel has an initial lumen diameter and is expandable to an enlarged lumen diameter, said implant comprising:
    a. a hollow rigid conduit having:
        i. a first portion and a second portion, said first portion sized to be larger than the initial lumen diameter and smaller than the enlarged lumen diameter, said second portion sized to extend from the first portion and through said myocardium into said chamber;
        ii. open first and second ends on respective ones of said first and second portions to define a blood flow pathway within an interior of said conduit between said first and second ends; and
        iii. at least the second portion of said conduit formed of a conduit material sufficiently rigid to resist deformation and closure of said pathway in response to contraction of said myocardium; and
    b. a stent having a first stent diameter and adapted to be enlarged to an enlarged second stent diameter, said stent in the first stent diameter sized to be inserted into said vessel when said lumen is at said initial lumen diameter, the second diameter sized to dilate the vessel to the enlarged lumen diameter and, when the stent is at the second stent diameter, the stent has an internal diameter sized to receive the first portion of the conduit.

2. An implant according to claim 1 wherein the stent is co-terminus with the first portion.

3. An implant according to claim 1 wherein the stent extends beyond the open first end of the first portion.

4. A method for establishing a blood flow path through a myocardium between a heart chamber and a lumen of a coronary vessel residing on an exterior of said myocardium where the vessel has an initial lumen diameter and is expandable to an enlarged lumen diameter, said method comprising:
    a. selecting a hollow rigid conduit having:
        i. a first portion and a second portion, said first portion sized to be larger than the initial lumen diameter and smaller than the enlarged lumen diameter, said second portion sized to extend from said first portion and through said myocardium into said chamber;
        ii. open first and second ends on respective ones of said first and second portions to define a blood flow pathway within an interior of said conduit between said first and second ends; and
        iii. at least the second portion of said conduit formed of a conduit material sufficiently rigid to resist deformation and closure of said pathway in response to contraction of said myocardium;
    b. selecting a stent having a first stent diameter and adapted to be enlarged to an enlarged second stent diameter, said stent in the first stent diameter selected to be inserted into said vessel when said lumen is at said initial enlarged lumen diameter and, when the stent is at the second stent diameter, the stent has an internal diameter sized to receive the first portion of the conduit;
    c. placing the second portion of the conduit through the myocardium with the second end in communication with the chamber;
    d. placing the stent in the first stent diameter into the vessel and enlarging the diameter of the stent to the second stent diameter to enlarge the diameter of the lumen; and
    e. placing the first portion of the conduit into the stent with the stent in the second diameter.

5. A method according to claim 4 comprising placing the first portion of the conduit in the stent with the stent and first portion being co-terminus.

6. A method according to claim 4 comprising placing the first portion of the conduit in the stent with the stent extending beyond the open first end of the first portion.

* * * * *